(12) United States Patent
McGuckin, Jr. et al.

(10) Patent No.: US 6,579,299 B2
(45) Date of Patent: *Jun. 17, 2003

(54) ATHERECTOMY DEVICE

(75) Inventors: James F. McGuckin, Jr., Radnor, PA (US); Peter W. J. Hinchliffe, Downington, PA (US); Walter H. Peters, Dowington, PA (US)

(73) Assignee: Rex Medical, L.P., Conshohocken, PA (US)

( * ) Notice: Subject to any disclaimer, the term of this patent is extended or adjusted under 35 U.S.C. 154(b) by 180 days.

This patent is subject to a terminal disclaimer.

(21) Appl. No.: 09/782,975

(22) Filed: Feb. 14, 2001

(65) Prior Publication Data

US 2001/0037121 A1 Nov. 1, 2001

Related U.S. Application Data

(63) Continuation-in-part of application No. 09/628,313, filed on Jul. 31, 2000, which is a continuation-in-part of application No. 29/117,719, filed on Jan. 31, 2000.

(51) Int. Cl.$^7$ ................................................ A61B 17/22
(52) U.S. Cl. ...................................... 606/159; 606/160
(58) Field of Search ................................. 606/159, 160, 606/167, 168, 170, 171, 79, 80, 180

(56) References Cited

U.S. PATENT DOCUMENTS

| 4,038,985 A | * | 8/1977 | Chiulli ....................... 606/159 |
| 4,445,509 A | | 5/1984 | Auth |
| 4,646,736 A | | 3/1987 | Auth |
| 4,664,112 A | | 5/1987 | Kensey et al. |
| 4,990,134 A | | 2/1991 | Auth |
| 5,019,088 A | | 5/1991 | Farr |
| 5,100,426 A | | 3/1992 | Nixon |
| 5,217,474 A | | 6/1993 | Zacca et al. |
| 5,267,955 A | | 12/1993 | Hanson |
| 5,308,354 A | * | 5/1994 | Zacca et al. ................. 606/159 |
| 5,318,576 A | | 6/1994 | Plassche, Jr. et al. |
| 5,489,291 A | | 2/1996 | Wiley |

(List continued on next page.)

FOREIGN PATENT DOCUMENTS

| DE | 19639193 | 4/1998 |
| WO | 9612453 | 5/1996 |
| WO | 9838928 | 9/1998 |

OTHER PUBLICATIONS

Medi–tech Boston Scientific Brochure, Rotatablator* Rotational Angioplasty System brochure, 1997.

*Primary Examiner*—Gloria M. Hale
(74) *Attorney, Agent, or Firm*—Neil D Gershon

(57) ABSTRACT

A surgical apparatus for removing deposits from an interior of a vessel comprising a rotatable shaft and a rotatable tip mounted to the rotatable shaft which is rotatable about its longitudinal axis upon rotation of the shaft to remove deposits from the interior of the vessel. The tip has a distal portion, a proximal portion and an intermediate portion between the distal and proximal portions. The intermediate portion is defined by a plurality of transverse cross-sectional areas, wherein each transverse cross-sectional area defines first and second axes substantially perpendicular to each other to define a width dimension along a first axis and a height dimension along the second axis. The height dimension is greater than the width dimension.

23 Claims, 15 Drawing Sheets

U.S. PATENT DOCUMENTS

| | | |
|---|---|---|
| 5,507,761 A | 4/1996 | Duer |
| 5,556,405 A | 9/1996 | Lary |
| 5,584,843 A | 12/1996 | Wulfman et al. |
| 5,632,755 A | 5/1997 | Nordgren et al. |
| D381,747 S | 7/1997 | Kapec et al. |
| 5,649,941 A * | 7/1997 | Lary .................... 606/159 |
| 5,681,336 A | 10/1997 | Clement et al. |
| D390,955 S | 2/1998 | Sjostrom et al. |
| 5,873,905 A * | 2/1999 | Plaia et al. .................. 623/1 |
| 5,897,566 A | 4/1999 | Shturman et al. |
| 5,938,670 A | 8/1999 | Keith et al. |
| 6,007,533 A | 12/1999 | Casscells et al. |
| 6,015,420 A | 1/2000 | Wulfman et al. |
| 6,080,170 A | 6/2000 | Nash et al. |
| 6,080,171 A * | 6/2000 | Keith et al. .................. 606/159 |
| 6,096,054 A | 8/2000 | Wyzgala et al. |
| 6,146,395 A * | 11/2000 | Kanz et al. .................. 606/159 |
| 6,156,048 A * | 12/2000 | Wulfman et al. ........... 606/159 |
| 6,165,187 A | 12/2000 | Reger |
| 6,183,487 B1 | 2/2001 | Barry et al. |
| 6,206,898 B1 | 3/2001 | Honeycutt et al. |
| 6,416,526 B1 * | 7/2002 | Wyzgala et al. ............. 606/170 |

* cited by examiner

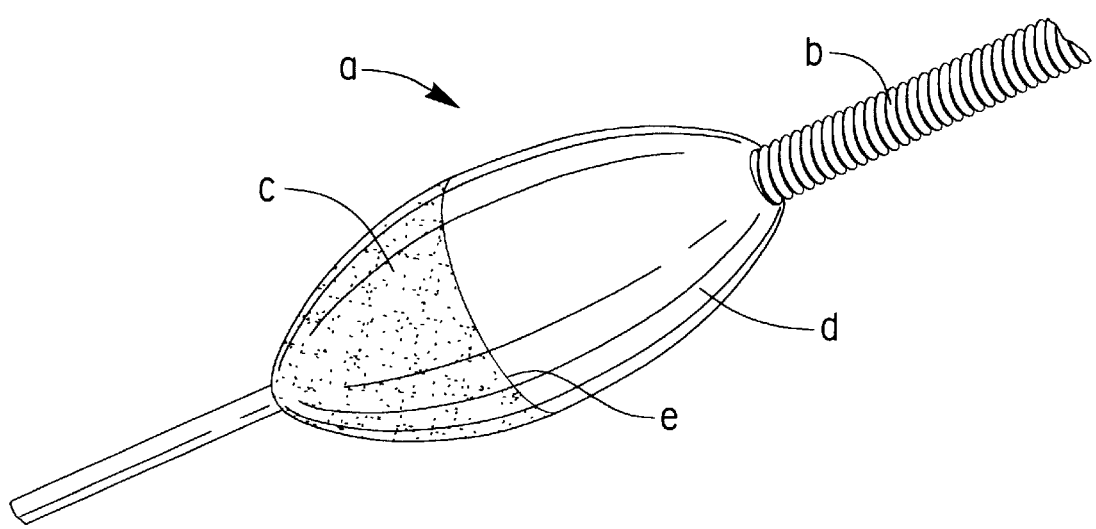
FIG_1
PRIOR ART

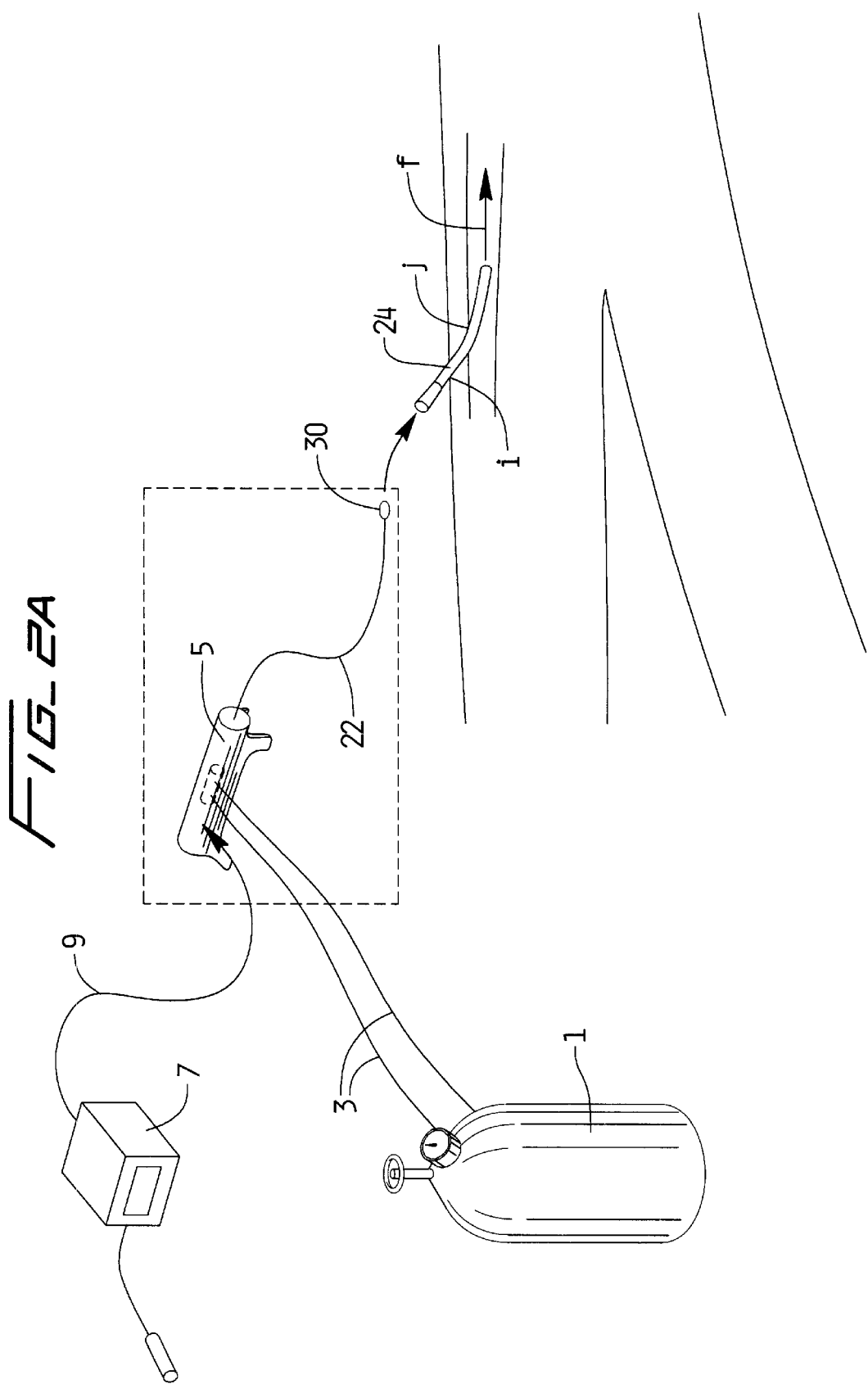

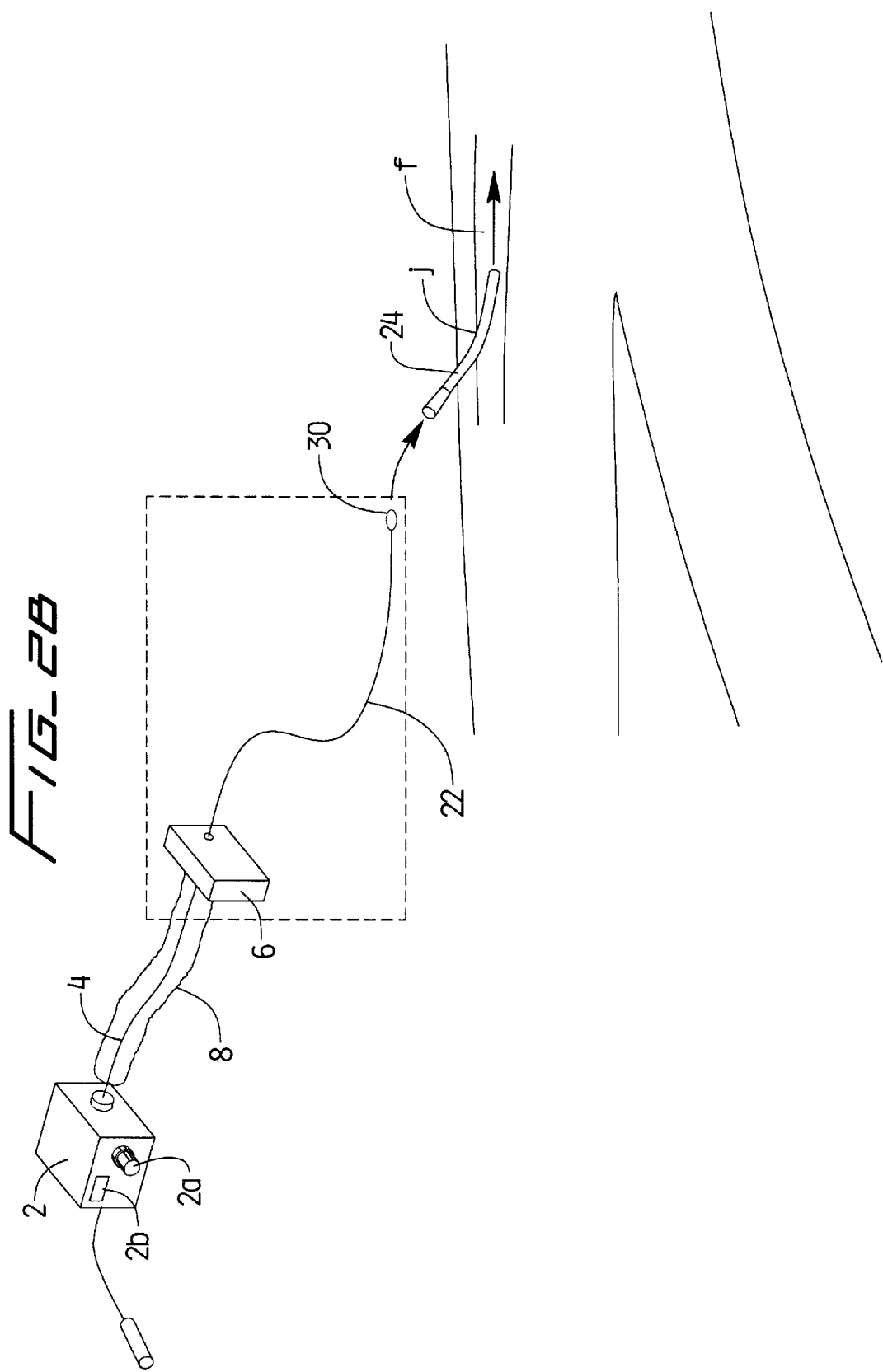

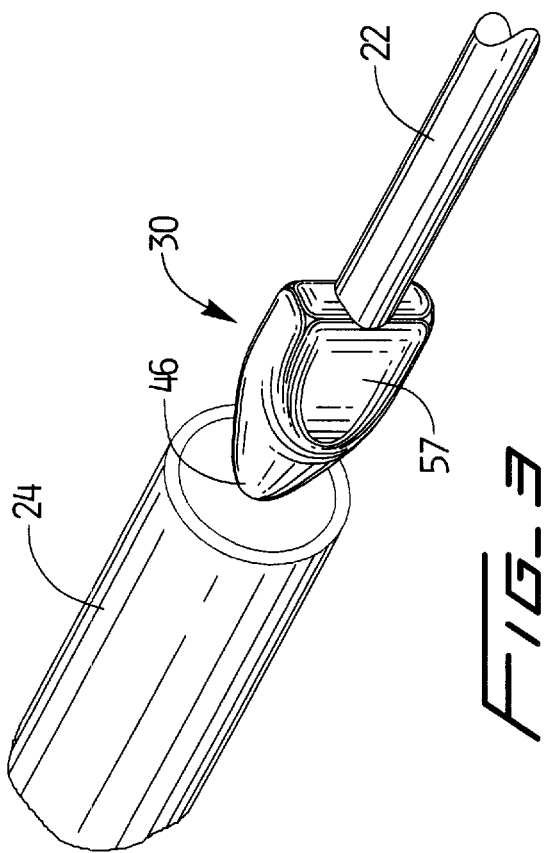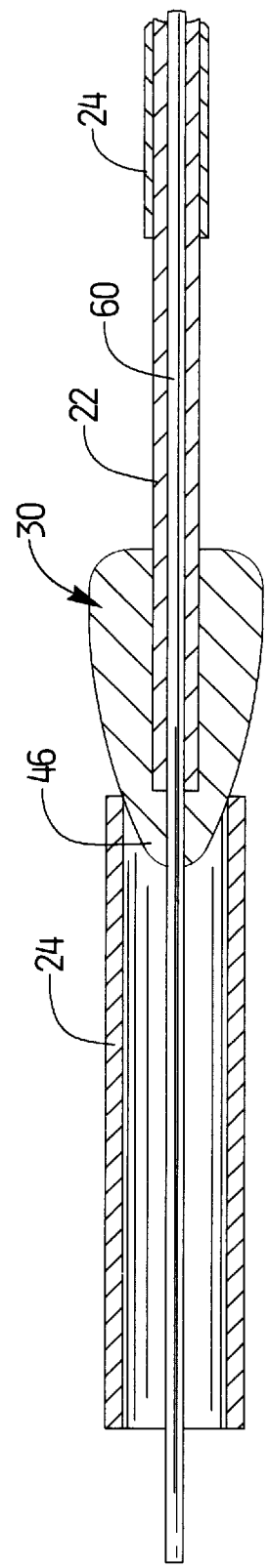

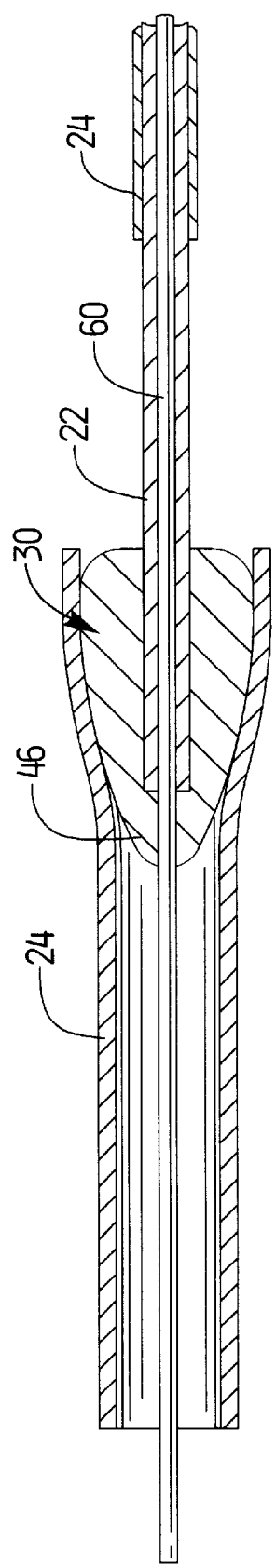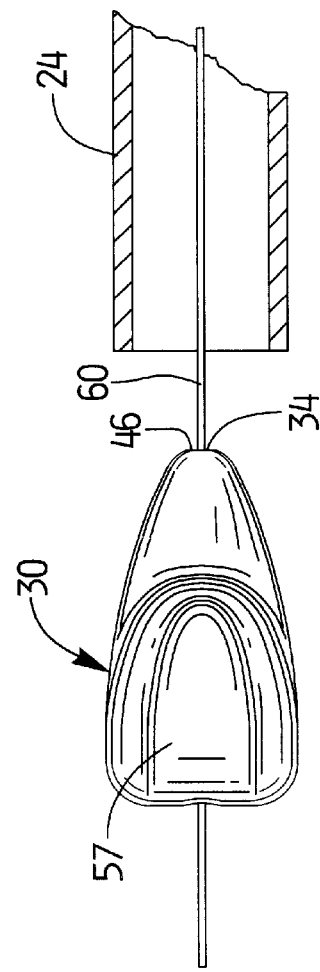

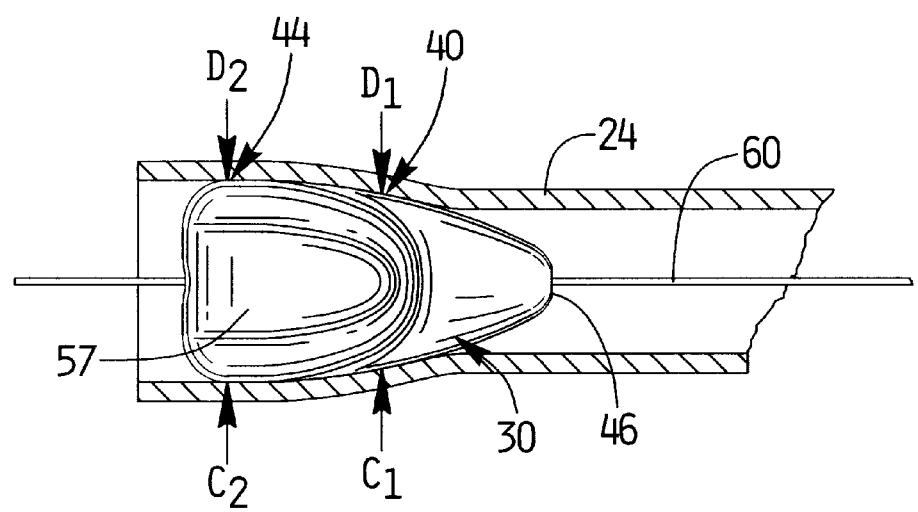
FIG_7
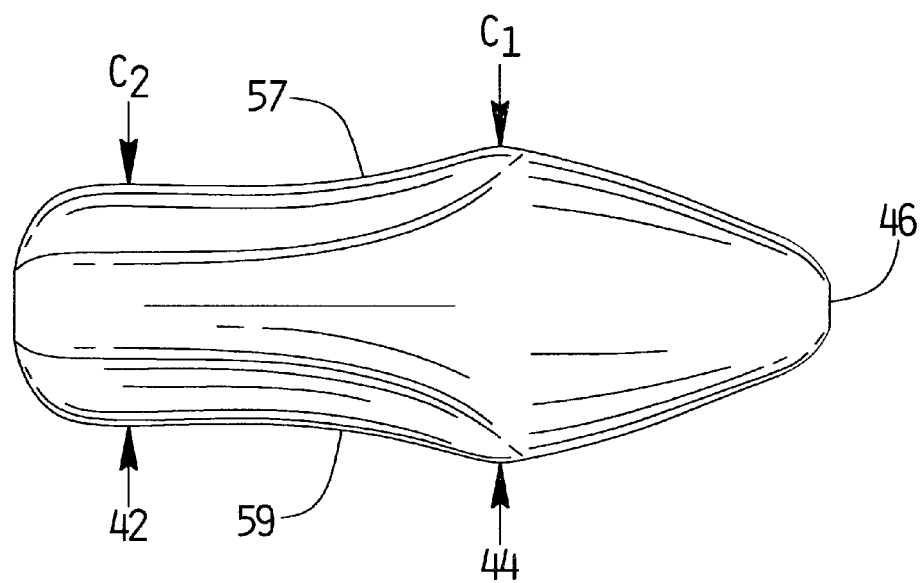
FIG_8

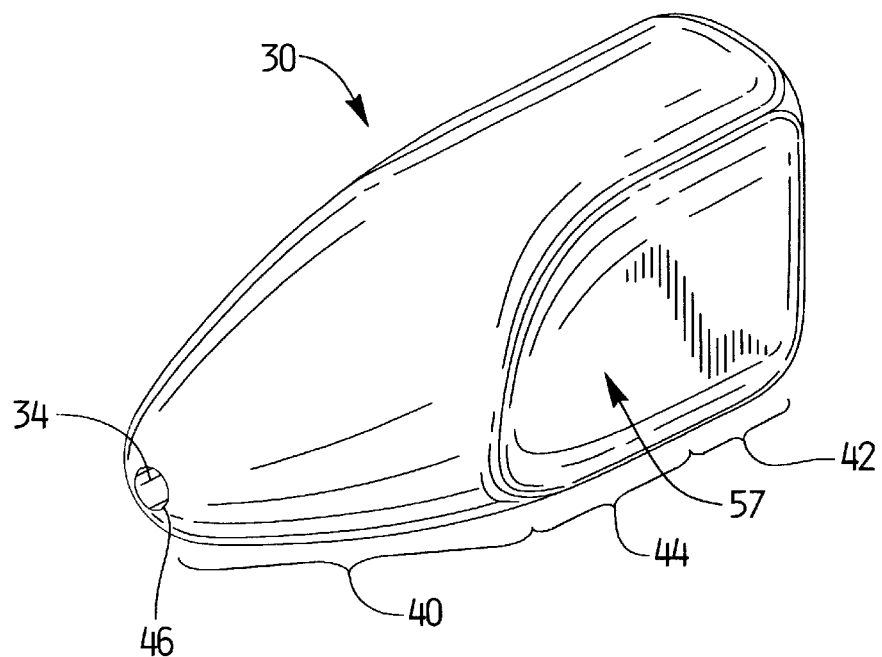
FIG_9
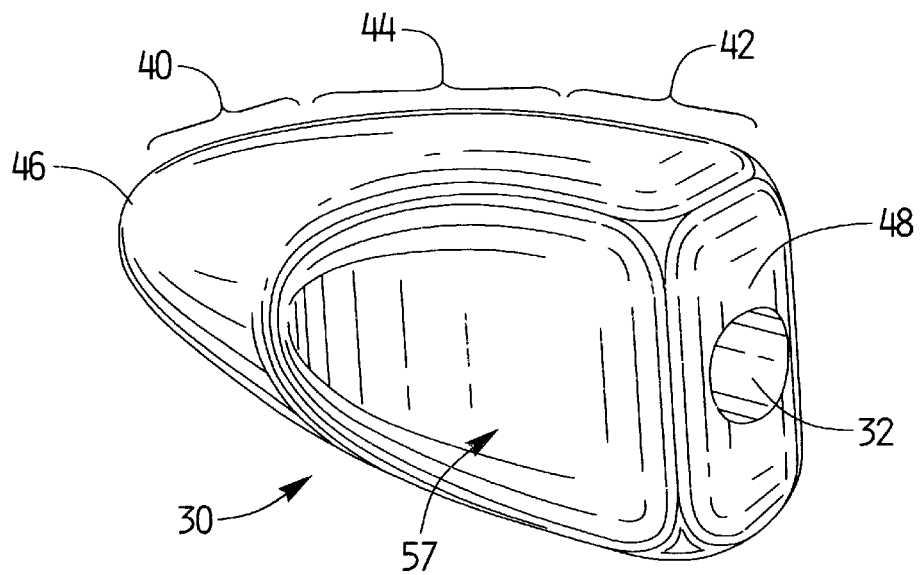
FIG_10

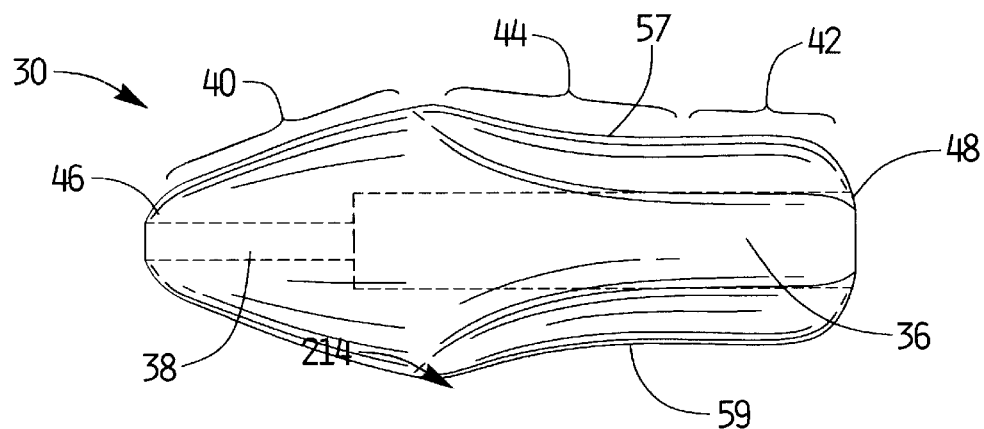
FIG_11
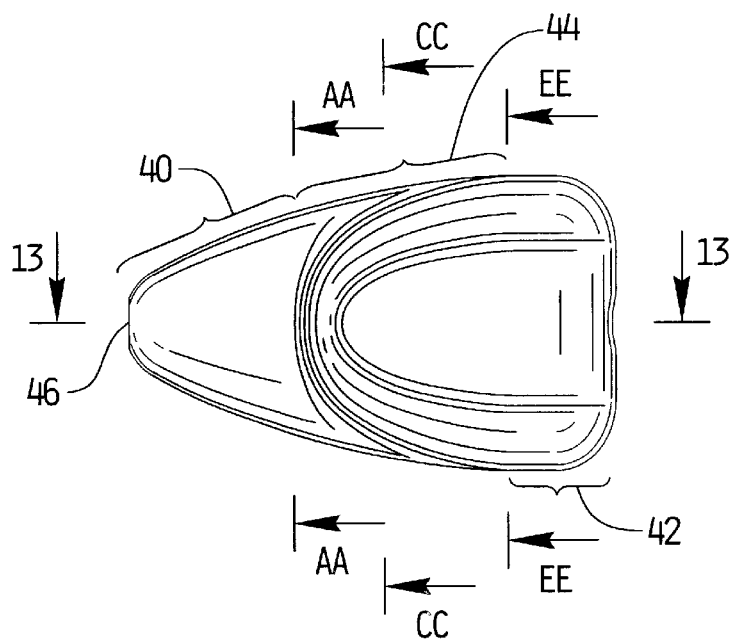
FIG_12
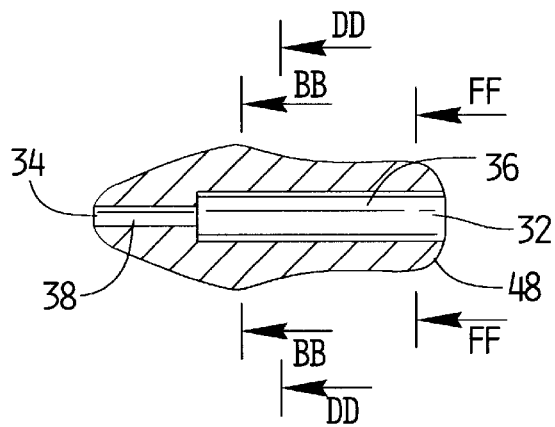
FIG_13

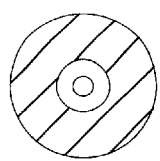
FIG_14A
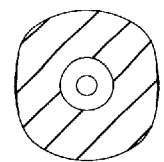
FIG_14B
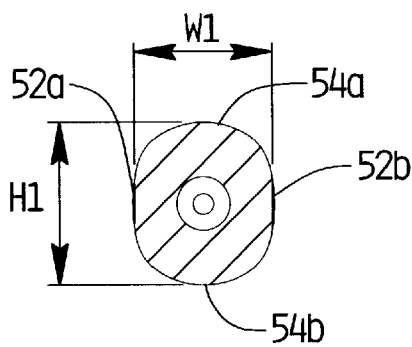
FIG_14C
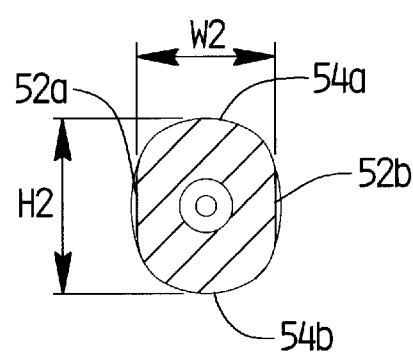
FIG_14D
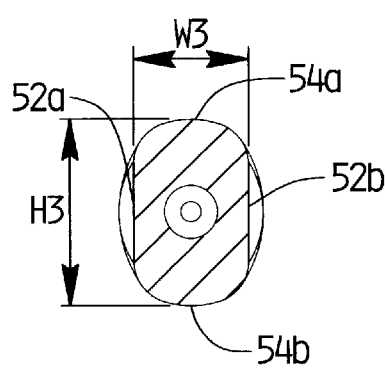
FIG_14E
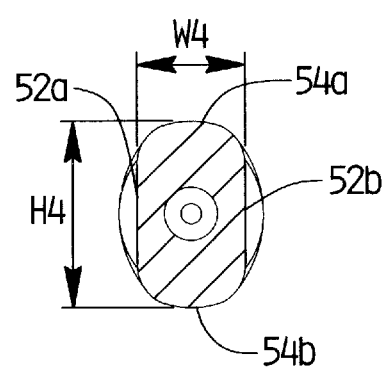
FIG_14F

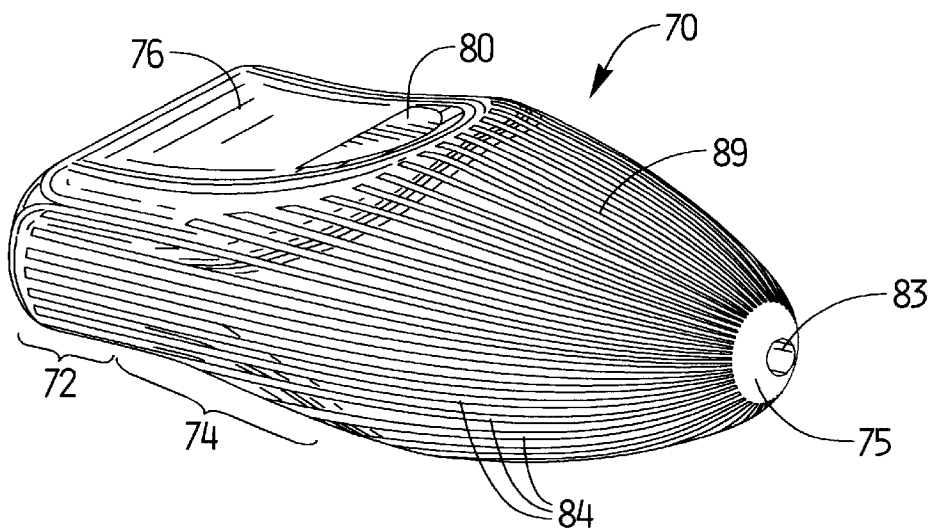
FIG_15A
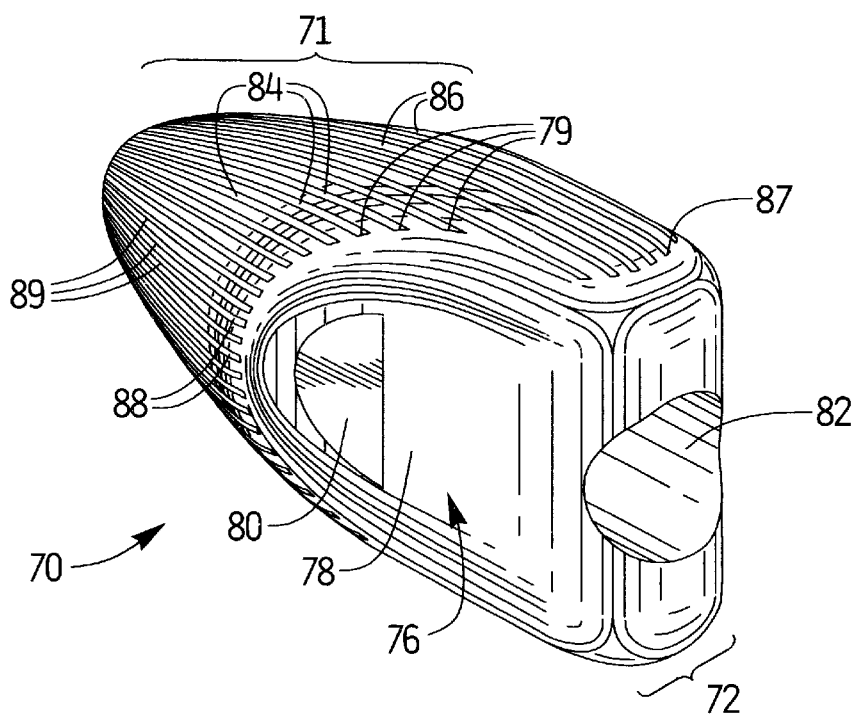
FIG_15B

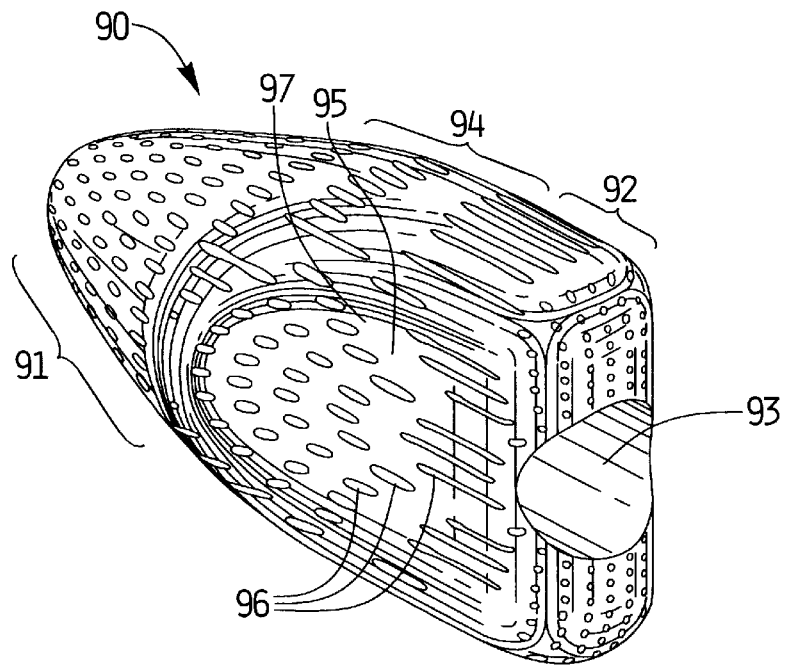
FIG_16
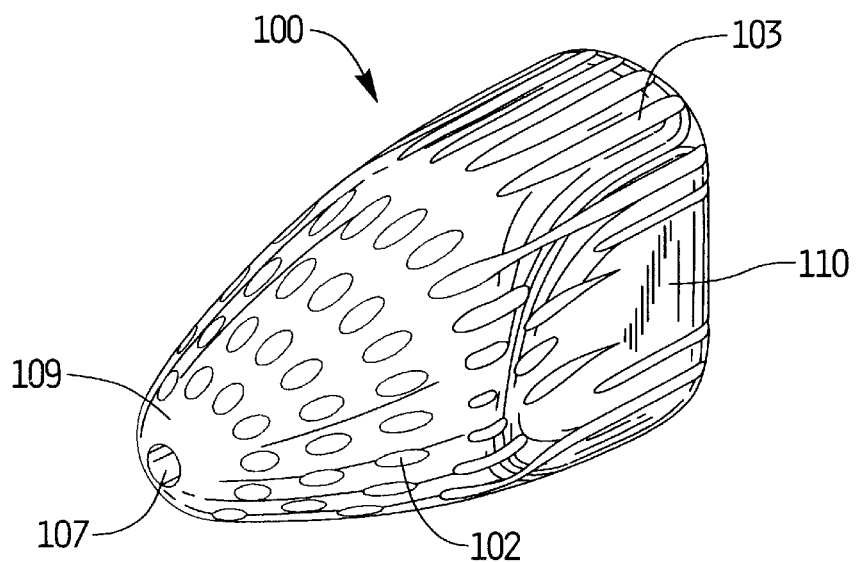
FIG_17A

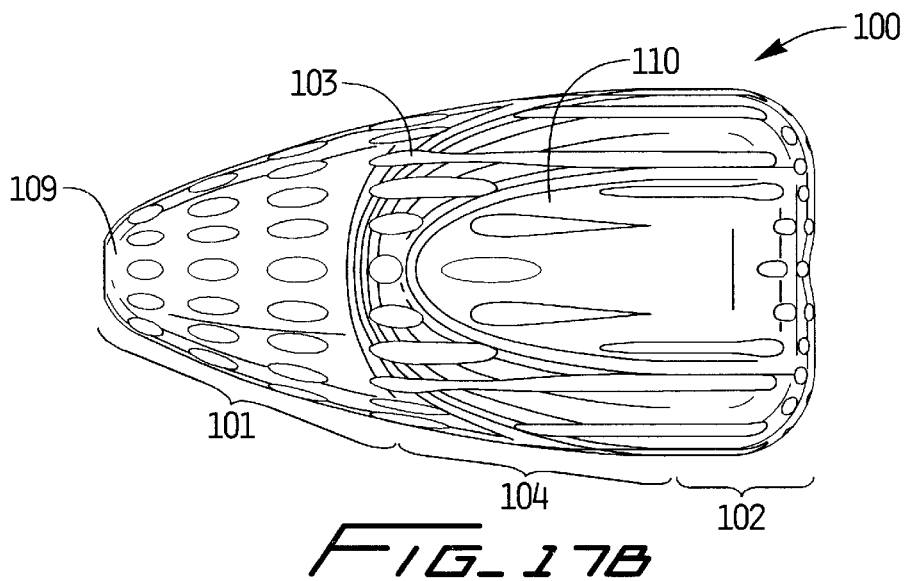
FIG_17B
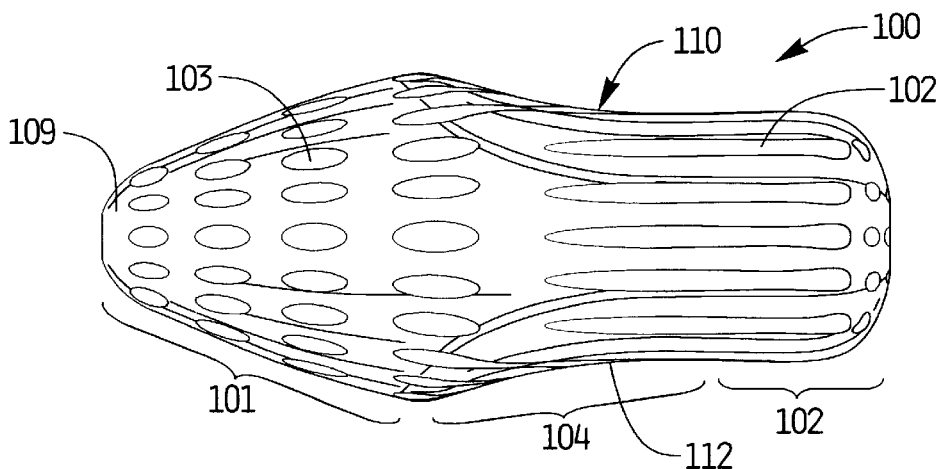
FIG_17C
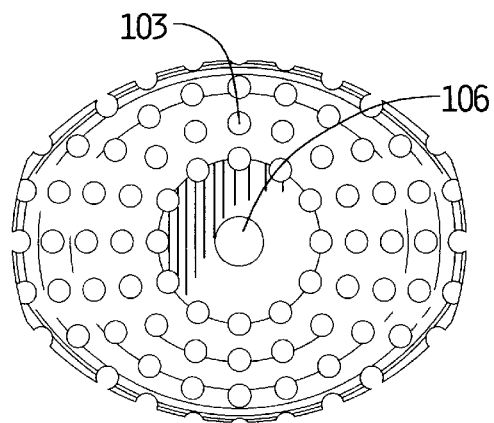
FIG_17D

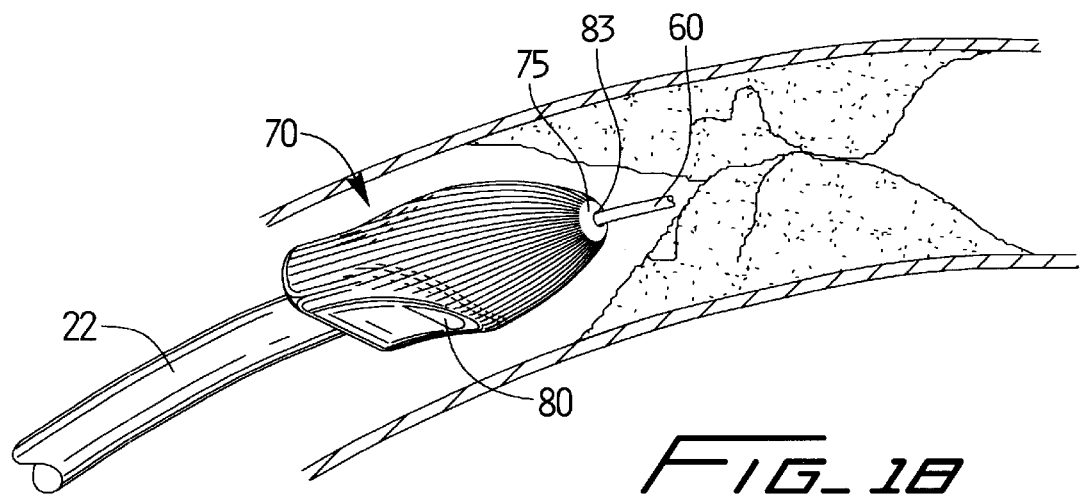
FIG_18
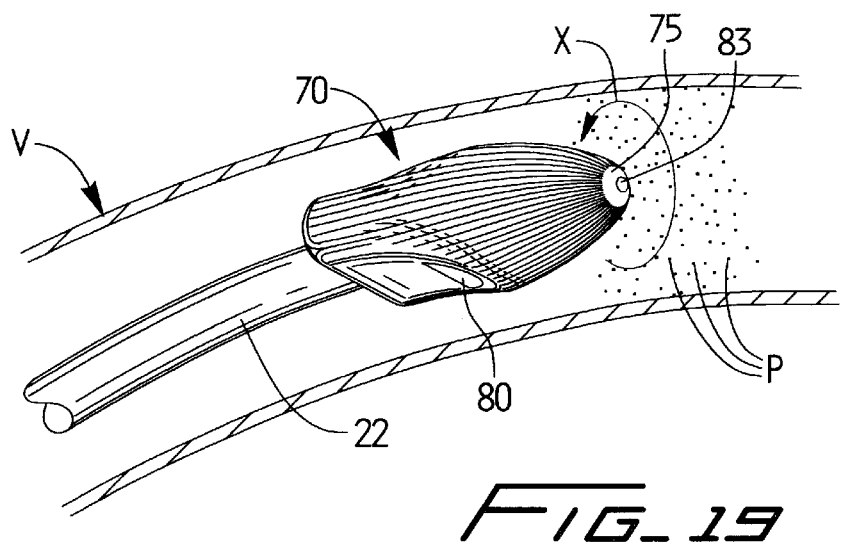
FIG_19
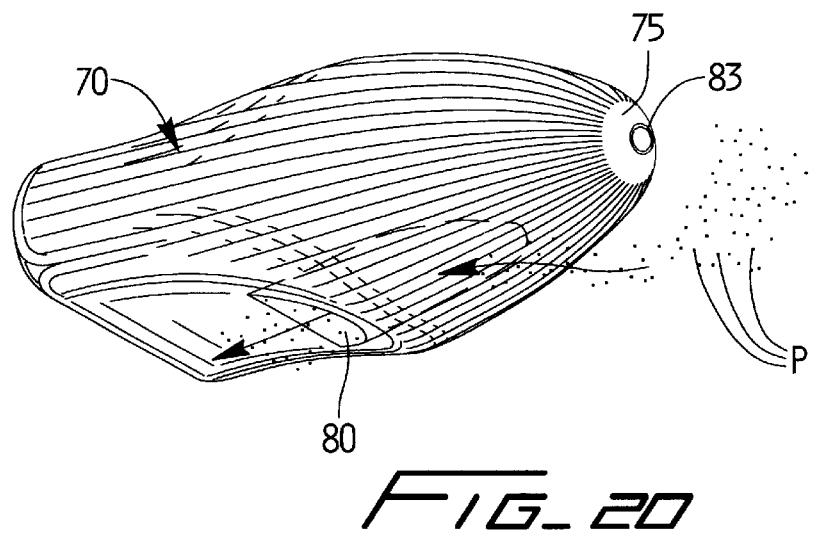
FIG_20

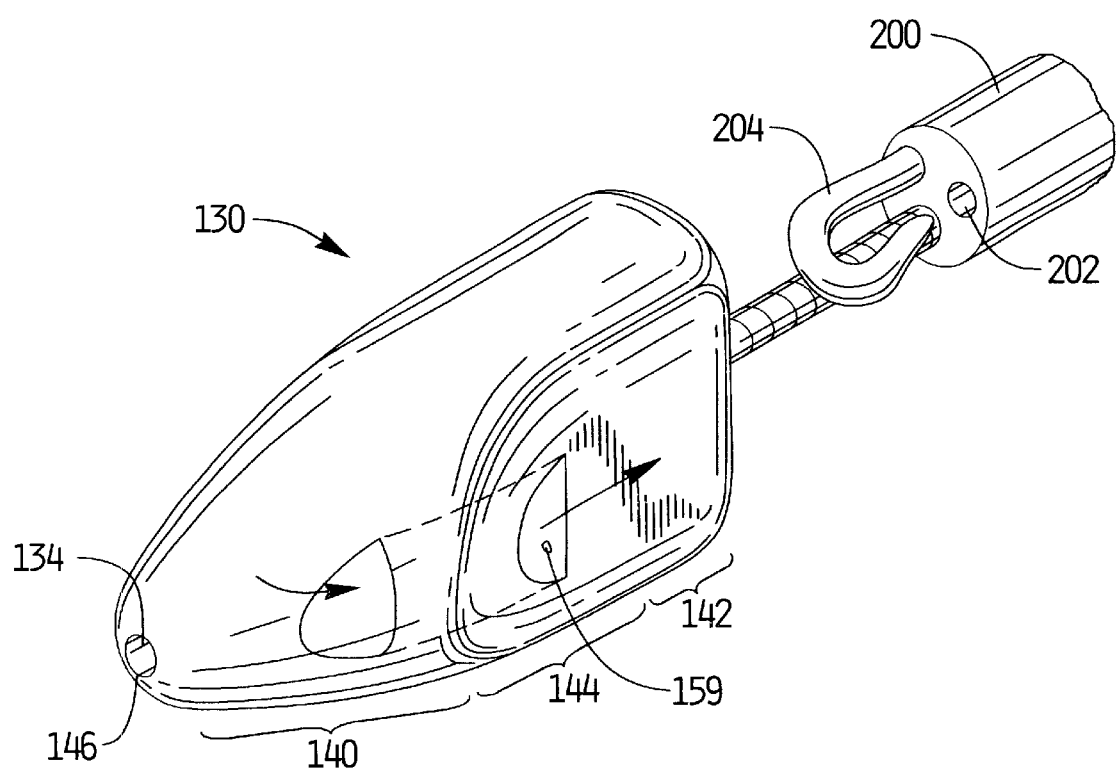
FIG_21

ATHERECTOMY DEVICE

BACKGROUND

This application is a continuation-in part of U.S. patent application 09/629,313, filed Jul. 31, 2000 which is a C-I-P of U.S. design application 29/117,719 filed Jan. 31, 2000, the contents of both applications are incorporated herein by reference.

TECHNICAL FIELD

This application relates to a vascular surgical apparatus, and more particularly to a minimally invasive device for removing plaque or other deposits from the interior of a vessel.

BACKGROUND OF RELATED ART

The vascular disease of atherosclerosis is the buildup of plaque or substances inside the vessel wall which reduces the size of the passageway through the vessel, thereby restricting blood flow. Such constriction or narrowing of the passage in the vessel is referred to as stenosis. In the case of peripheral vascular disease, which is atherosclerosis of the vascular extremities, if the vessel constriction is left untreated, the resulting insufficient blood flow can cause claudication and possible require amputation of the patient's limb. In the case of coronary artery disease, if left untreated, the blood flow through the coronary artery to the myocardium will become inadequate causing, myocardial infarction and possibly leading to stroke and even death.

There are currently several different treatments for treating arterial disease. The most invasive treatment is major surgery. With peripheral vascular diseases, such as occlusion of the tibial artery, the major surgery involves implantation and attachment of a bypass graft to the artery so the blood flow will bypass the occlusion. The surgery involves a large incision, e.g. a 10 inch incision in the leg, is expensive and time consuming for the surgeon, increases patient pain and discomfort, results in a long patient recovery time, and has the increased risk of infection with the synthetic graft.

Major surgery for treating coronary artery disease is even more complex. In this surgery, commonly referred to as open heart surgery, a bypass graft connects the heart to the vessel downstream of the occlusion, thereby bypassing the blockage. Bypass surgery requires opening the patient's chest, is complex, has inherent risks to the patient, is expensive and requires lengthy patient recovery time. Bypass surgery also requires use of a heart lung machine to pump the blood as the heart is stopped, which has its own risks and disadvantages. Oftentimes, the saphenous vein in the patient's leg must be utilized as a bypass graft, requiring the additional invasive leg incision which further complicates the procedure, increases surgery time, lengthens the patient's recovery time, can be painful to the patient, and increases the risk of infection.

Attempts to minimize the invasiveness of coronary bypass surgery are currently being developed and utilized in certain instances. These typically include cracking a few ribs and creating a "window approach" to the heart. Although the window approach may reduce patient trauma and recovery time relative to open heart surgery, it still requires major surgery, and is a complicated and difficult surgery to perform due to limited access and limited instrumentation for successfully performing the operation. Attempts to avoid the use of a heart lung machine by using heart stabilization methods is becoming more accepted, but again, this does not avoid major surgery.

Due to these problems with major peripheral or coronary vascular surgery, minimally invasive procedures have been developed. Balloon angioplasty is one of the minimally invasive methods for treating vessel occlusion/obstructions. Basically, a catheter having a balloon is inserted through the access artery, e.g. the femoral artery in the patient's leg or the radial artery in the arm, and advanced through the vascular system to the occluded site over a wire. The deflated balloon is placed at the occlusion and the balloon is inflated to crack and stretch the plaque and other deposits to expand the opening in the vessel. Balloon angioplasty, especially in coronary surgery, is frequently immediately followed by insertion of a stent, a small metallic expandable device which is placed inside the vessel wall to retain the opening which was created by the balloon. Balloon angioplasty has several drawbacks including difficulty in forcing the balloon through the partially occluded passageway if there is hard occlusion, the risk involved in cutting off blood flow when the balloon is fully inflated, and the frequency of restenosis after a short period of time since the plaque is essentially stretched or cracked and not removed from the vessel wall or because of the development of intimal hyperplasia.

Another minimally invasive technique used to treat arteriosclerosis is referred to as atherectomy and involves removal of the plaque by a cutting or abrading instrument. This technique provides a minimally invasive alternative to bypass surgery techniques described above as well as can provide an advantage over balloon angioplasty methods in certain instances. Atherectomy procedures typically involve inserting a cutting or ablating device through the access artery, e.g. the femoral artery or the radial artery, and advancing it through the vascular system to the occluded region, and rotating the device at high speed to cut through or ablate the plaque over the wire. The removed plaque or material can then be suctioned out of the vessel or be of such fine diameter that it is cleared by the reticuloendothelial system. Removal of the plaque in an atherectomy procedure has an advantage over balloon angioplasty plaque displacement since it debulks the material.

Examples of atherectomy devices in the prior art include U.S. Pat. Nos. 4,990,134, 5,681,336, 5,938,670, and 6,015,420. These devices have elliptical shaped tips which are rotated at high speeds to cut away the plaque and other deposits on the interior vessel wall. A well-known device is marketed by Boston Scientific Corp. and referred to as the Rotablator. As can be appreciated, in these devices, the region of plaque removal is dictated by the outer diameter of the cutting tip (burr) since only portions of the plaque contacted by the rotating tip are removed. Obviously, the greater the area of plaque removed, the larger passageway created through the vessel and the better the resulting blood flow.

Since these atherectomy tips need to be inserted through an introducer sheath or catheter to the target site, the larger the tip, the larger the diameter of the introducer sheath required. However, larger introducer sheaths increase the risk of trauma to the patient, are harder to navigate through the vessels, and create larger incisions (require larger puncture sites) into the access artery which cause additional bleeding and complicate closure of the incision at the end of the procedure. On the other hand, if the introducer sheath is too small, then the rotating tip will not be able to remove a sufficient area of obstructive deposits and the vessel will remain partially occluded. Thus, a tradeoff must be made between these two opposing goals: larger cutting tip but smaller introducer sheath.

This problem was recognized for example in U.S. Pat. Nos. 5,217,474 and 6,096,054 which attempted solutions involved expandable cutting tips. These tips however are quite complex and require additional expansion and contraction steps by the surgeon.

The need therefore exists to provide an improved atherectomy cutting tip to obtain an optimal balance between the competing objectives of the smallest introducer sheath size to facilitate insertion and reduce trauma to the vessel and the largest atherectomy tip size to remove a larger region of plaque or other deposits from the vessel wall.

SUMMARY

The present invention provides a uniquely configured atherectomy tip which enables a smaller sized introducer sheath to be utilized without sacrificing the region of plaque being removed from the interior of the vessel.

More specifically, the present invention provides a surgical apparatus for removing deposits from an interior of a vessel comprising a rotatable shaft and a rotatable tip mounted to the shaft and rotatable about its longitudinal axis upon rotation of the shaft to remove deposits from the interior of the vessel. The tip has a distal portion, a proximal portion and an intermediate portion between the distal and proximal portions. The intermediate portion is defined by a plurality of transverse cross-sectional areas, wherein each transverse cross-sectional area defines first and second axes substantially perpendicular to each other to define a width dimension along the first axis and a height dimension along the second axis. The height dimension is greater than the width dimension.

Preferably, the height progressively increases towards the proximal portion and the width progressively decreases toward the proximal portion. An opening in a sidewall of the tip for removal of the cut plaque can be provided. The distal portion may have a bullet shaped nose. A plurality of longitudinally extending grooves or cutouts can be formed in an outer surface of the tip to form an ablation surface.

The present invention also provides a surgical apparatus for removing deposits such as plaque from an interior of a vessel, comprising a rotatable shaft having a lumen extending therethrough dimensioned to receive a guidewire and a tip mounted on the rotatable shaft for rotation about its longitudinal axis upon rotation of the shaft. The tip has a distal portion, a proximal portion and an intermediate portion between the distal and proximal portions. The tip includes a guidewire lumen for receiving a guidewire to enable over the wire insertion of the shaft and tip. The distal portion of the tip is substantially circular in cross-section and the intermediate and proximal portions are non-circular in cross-section.

Preferably, the non-circular cross-section of the intermediate and proximal portions is defined by first and second opposing walls separated by a first distance and third and fourth opposing walls separated by a second distance, wherein the first distance is greater than the second distance. The first distance preferably progressively increases towards the proximal portion and the second distance progressively decreases towards the proximal portion. The third and fourth walls preferably have a substantially linear portion and the first and second walls are preferably curved.

The present invention also provides a vascular surgical apparatus for removing deposits such as plaque from a vessel comprising a rotatable shaft with a distal section and a distal tip mounted on the distal section and rotatable upon rotation of the shaft to remove deposits in a circumferential area determined by a major diameter of the distal tip as it rotates on its axis. The distal tip has a proximal portion, a distal portion and an intermediate portion between the proximal and distal portions, wherein each transverse cross-section of the tip defines a circumference, a first diameter, and a second diameter substantially orthogonal to the first diameter. The first diameter of the intermediate portion is greater than the first diameter of the distal portion and the circumference at the distal portion is substantially equal to the circumference at the intermediate portion.

Preferably, the first diameter of the intermediate portion is greater than a second diameter of the intermediate portion and the first diameter of the distal portion is substantially equal to the second diameter of the distal portion. The intermediate portion has opposing scalloped portions to form the smaller second diameter region.

A method for removing deposits from an interior of a vessel is also provided comprising the steps of:

providing an introducer sheath having a first internal diameter;

providing a deposit removal tip having a rotating shaft and a rotating tip at the distal end of the shaft, the rotating tip having an outer diameter greater than the internal diameter of the sheath and further having first and second opposing narrowed regions;

inserting the introducer sheath through a skin incision and into a vessel, the sheath forming an incision opening at least equal to the external diameter of the sheath;

inserting the rotating tip into the introducer sheath to deform the introducer sheath to accommodate the larger outer diameter of the rotating tip;

moving the tip out through a distal opening in the introducer sheath, thereby allowing the introducer sheath to return to its undeformed configuration;

advancing the distal tip adjacent the deposits to be removed; and rotating the tip at high speed to contact and remove the deposits from the interior of the vessel.

BRIEF DESCRIPTION OF THE DRAWINGS

Preferred embodiment(s) of the present disclosure are described herein with reference to the drawings wherein:

FIG. 1 is a perspective view of a prior art atherectomy device having a symmetrical elliptical configuration;

FIG. 2A is a schematic view of a gas powered system for rotating the atherectomy tip (burr) of the present invention;

FIG. 2B is schematic view of an electrically powered system for rotating the atherectomy tip (burr) of the present invention;

FIG. 3 is a perspective view of a first embodiment of the atherectomy device of the present invention prior to insertion through an introducer sheath;

FIG. 4 is a cross-sectional view of the atherectomy device of FIG. 3 shown partially inserted into the introducer sheath;

FIG. 5 is a cross-sectional view of the atherectomy device of FIG. 3 shown fully inserted into the introducer sheath to deform the sheath FIG. 6 is a side view of the atherectomy tip of FIG. 3 (the shaft removed for clarity) shown inserted over the guidewire and prior to insertion within the introducer sheath;

FIG. 7 is a partial cross-sectional view showing the atherectomy tip of FIG. 3 (the shaft removed for clarity)

Figure 2C:
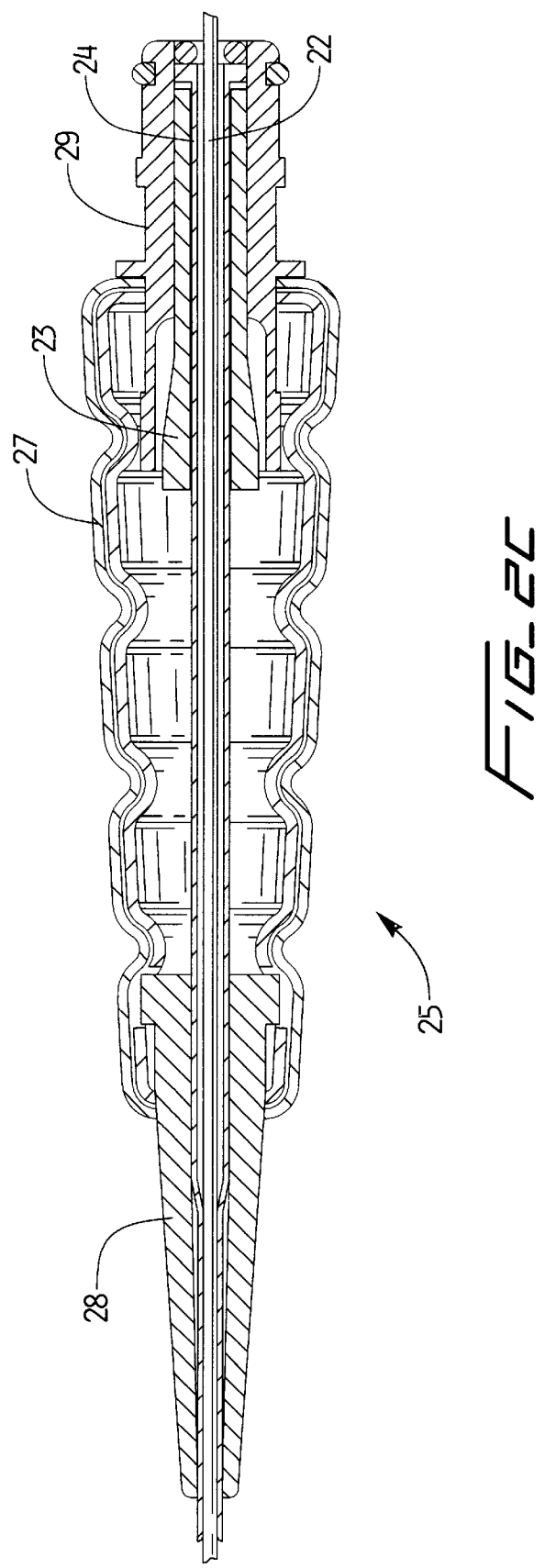
FIG. 2C is a cross-sectional view illustrating the connection to the drive unit of FIG. 2B.

inserted into the introducer sheath to deform the sheath, and further showing the circumference and diameter relationships of the tip;

FIG. 8 is a top view of the atherectomy tip of FIG. 3 showing the circumference at the intermediate and proximal portions;

FIG. 9 is a front perspective view of the atherectomy tip of FIG. 3;

FIG. 10 is a rear perspective view of the atherectomy tip of FIG. 3;

FIG. 11 is a top view of the atherectomy tip of FIG. 3;

FIG. 12 is side view of the atherectomy tip of FIG. 3;

FIG. 13 is a longitudinal cross section view of the atherectomy tip of FIG. 3 taken along lines A—A of FIG. 12;

FIGS. 14A, 14B, 14C, 14D, 14E and 14F are transverse cross-sectional views taken along lines AA, BB, CC, DD, EE and FF, respectively, of FIGS. 12 or 13 as shown;

FIG. 15A is a side perspective view of an alternate embodiment of the atherectomy tip of the present invention having a plurality of longitudinal grooves formed in the outer surface;

FIG. 15B is a rear perspective view of the atherectomy tip of FIG. 15;

FIG. 16 is a rear perspective view of another alternate embodiment of the atherectomy tip having a plurality of variously shaped cutouts formed in the outer surface;

FIG. 17A is a front perspective view of yet another alternate embodiment of the atherectomy tip of the present invention having a plurality of indentations formed by a laser cutting technique;

FIG. 17B is a side view of the atherectomy tip of FIG. 17A;

FIG. 17C is a top view of the atherectomy tip of FIG. 17A;

FIG. 17D is a front view of the atherectomy tip of FIG. 17A;

FIG. 18 is a perspective view of the atherectomy device of FIG. 15 inserted over a guidewire into a vessel for removing plaque;

FIG. 19 illustrates rotation of the atherectomy tip of FIG. 15 to remove plaque within the vessel;

FIG. 20 is a perspective view showing the debris removed through the side port of the atherectomy tip of FIG. 15, the shaft and the vessel removed for clarity; and FIG. 21 is a perspective view of an alternate embodiment of the atherectomy tip of FIG. 9 shown having side ports to facilitate removal by the illustrated suction apparatus.

DETAILED DESCRIPTION OF PREFERRED EMBODIMENTS

The present invention is directed to an atherectomy tip designed for high speed rotation to remove plaque or other deposits on the inside wall of the vessel to widen the blood passageway therethrough. To achieve such rotation, the atherectomy tip is positioned at a distal end of a flexible rotating shaft that can be gas or electrically powered as described below. The shaft rotates at high speed, typically between 100,000 and 200,000 rpm, causing the cutting or ablation surface of the tip to remove the plaque and deposits to which it comes into contact. The atherectomy tip of the present invention has application in a variety of vessels such as the coronary arteries, peripheral vessels such as the tibial artery, femoral, and popliteal, and saphenous vein bypass grafts.

In order for the atherectomy tip to reach the vessel stenosis (obstruction) it is inserted along with the flexible shaft through an introducer sheath and over a guidewire. More specifically, the introducer sheath is placed through a skin incision and into a vessel, e.g. the femoral artery in the patient's leg, to provide access to the target site. A guidewire is then inserted through the introducer sheath and advanced through the appropriate vessels to the target obstructed site, typically the coronary artery. The flexible shaft and attached atherectomy tip are then inserted through the introducer sheath and threaded over the length of the guidewire to the target obstructed site. Actuation of the system spins the shaft and tip so the cutting surface repeatedly comes into contact with the obstruction, e.g. plaque, to remove it from the vessel wall. The systems for causing rotation of the shaft and tip are not part of the present invention, but are illustrated for convenience in FIGS. 2A and 2B, discussed below.

The atherectomy tip of the present is advantageously uniquely configured for placement through a smaller sized introducer sheath without sacrificing the region of plaque it is capable of removing. This is uniquely achieved through the circumferential and diametrical relationship of the tip at various sections along its length which will be explained in detail below. The advantages of utilizing a smaller sized sheath, as enumerated above in the Background Section of this application, are it is less traumatic to the vessel, reduces the amount of bleeding, reduces the risk of infection and eases closure of the vessel at the end of the procedure.

In order to better understand the unique configuration and dimensional relationship of the atherectomy tip of the present invention, a brief discussion of a prior art device is provided in conjunction with FIG. 1. FIG. 1 illustrates the prior art atherectomy tip or burr referred to as the "Rotablator" and sold by Medi-Tech (Boston Scientific Corporation). Atherectomy tip "a" is attached to flexible rotation shaft "b", and is elliptical in shape as shown. Its leading or distal portion "c" progressively increases in diameter toward an intermediate portion "e" and its trailing or proximal portion "d" progressively decreases in diameter away from the intermediate portion "e". The tip "a" is circular in transverse cross-section at all regions along its length. Consequently, at each transverse "slice" of the tip, the diameter is uniform in all directions. The circumference of the tip at each transverse slice likewise increases from the distal to the intermediate portion and decreases from the intermediate to the proximal portion.

At the intermediate portion "e", the prior art tip "a" is at its greatest diameter and has its greatest circumference. Since the tip is inserted through an introducer sheath as explained above, the internal dimensions of the sheath must accommodate this largest diameter region of the tip. Thus, the internal diameter of the sheath must be at least slightly larger than the largest outer diameter of the tip "a" to accommodate the tip. Another way to view this is that the internal lumen of the sheath must be at least slightly larger than the largest transverse circumferential region of the tip. Since the inner diameter of the sheath must be greater than the tip diameter, the outer diameter is even larger because the sheath must have sufficient wall thickness for stability and to prevent kinking during insertion of the instrumentation. The outer diameter of the sheath dictates the size of the incision required through the skin and the vessel.

The prior art atherectomy tips "a" are provided in various sizes, each requiring insertion through an appropriately sized introducer sheath. Chart I below provides examples of the conventional sheath sizes required for the various sized prior art atherectomy tips of FIG. 1. The tip diameter corresponds to the largest diameter of the tip, i.e. at the intermediate section "e" identified above, since the entire tip must fit through the sheath. The sheath diameters reflect conventional sheaths currently being utilized in the industry.

CHART I

| Tip Diameter | Sheath Diameter |
|---|---|
| 1.5 mm | 5 French (1.67 mm) |
| 2.0 mm | 7 French (2.3 mm) |
| 2.5 mm | 8 French (2.7 mm) |
| 3.0 mm | 10 French (3.3 mm) |

As can be appreciated from Chart I, the atherectomy tip of the prior art requires a sheath size which is greater in diameter than the tip diameter. The largest diameter of the tip also dictates the region of plaque which can be removed, since as the tip rotates at high speeds, it only cuts the plaque which comes into contact with the outermost surface.

The present invention will now be described with detailed reference to the drawings wherein like reference numerals identify similar or like components throughout the several views. However, for background, the system for rotating the atherectomy tip or burr of the present invention will first be discussed.

FIGS. 2A and 2B illustrate schematically alternative systems for rotating the tip to ablate or cut plaque or other obstructions from inside the vessel to treat vessel stenosis (constriction or narrowing of the vessel opening). FIG. 2A illustrate a gas powered system with air lines 3 transporting air from air tank 1 to drive unit 5. Speedometer 7, connected to drive unit 5 via line 9, provides a visual indication of the rotational speed which is adjustable by adjusting the air feed. Flexible shaft or cable 22, extending from drive unit 5, has the atherectomy tip or burr 30 of the present invention at the distalmost end. High speed rotation of the shaft 22 likewise rotates tip 30, enabling the tip 30 to ablate plaque to treat stenosis of a vessel. The drive unit 5, flexible shaft 22 and tip 30, are preferably disposable as shown in broken lines in FIG. 2A.

FIG. 2A illustrates by the arrow, that the tip 30, and a portion of the shaft 22, are inserted through introducer sheath or catheter 24. As shown for illustrative purposes, introducer sheath is inserted through an incision "i" in the patient's leg, and through an incision "j" in the femoral artery "f". The shaft 22 and tip 30 are thus introduced through the sheath 24 into the femoral artery "f", and advanced to the target artery, e.g. the coronary artery to the treatment obstruction site. Note that a guidewire (not shown) extends through the sheath 24 and into the target artery so that the shaft 22 and tip 30 are inserted over the guidewire. The drive unit 5 includes an advancing mechanism (not shown) for sliding the shaft 22 and tip 30 a desired distance within the vessel (e.g. 3–10 cm).

FIG. 2B illustrates an alternate embodiment for causing rotation of the tip 30. A generator 2 is plugged into an A/C outlet and is electrically wired to drive unit 6. The cable or wire 4 is contained in an insulating sheath 8 which maintains sterility of wire 4. The flexible shaft 22, with burr or tip 30 at its distalmost end, is electrically powered for high speed rotation to rotate the shaft 22 and tip 30. Control knob 2a adjusts the rotational speed of the shaft 22 and tip 30, with window 2b visually displaying the speed. The drive unit includes an advancing mechanism (not shown) for sliding the shaft 22 and tip 30 a desired distance within the vessel (e.g. 3–10 cm). As shown in FIG. 2C, connector 25 includes a housing 27, flexible nose 28 and a connector housing 29 which connects to the drive unit. Introducer sheath 24, supported by tubing support 23, is contained within the connector housing 29. The drive unit 6, shaft 22 and tip 30 can be disposable as shown in broken lines in FIG. 2A. Alternatively, the drive unit 6, like the generator 2, can be reusable. The flexible shaft 22 with tip 30 is inserted through introducer sheath 24 in the femoral artery in the same manner as described above with respect to the embodiment of FIG. 2A. This catheter 24 is also illustrated in FIGS. 4 and 5.

It should be appreciated that the tip 30 in both FIGS. 2A and 2B is shown inserted through the femoral artery by way of example as other vessels can be utilized for access, such as the radial artery. Also the tip of the present invention can be used to remove plaque or other obstructions in a variety of vessels such as the coronary artery, the tibial artery, the superficial femoral, popliteal, saphenous vein bypass grafts and instent restenosis.

Turning now to FIGS. 3–14, a first embodiment of the atherectomy tip of the present invention will now be described. With initial reference to FIGS. 9–11, tip or burr, designated generally by reference numeral 30, has a front portion (section) 40, a rear portion (section) 42, and an intermediate portion (section 44). These portions vary in transverse cross-section as can be appreciated by reference to FIGS. 12–14. Thus, the front portion 40 can be defined for convenience as the area starting at the distalmost tip 46, terminating at the cross-sectional line AA of FIG. 12, and forming a bullet-nose configuration. The cross-section is substantially circular in configuration.

Intermediate portion 44 can be considered for convenience as starting at section line AA and terminating near section line EE. The cross-section of the intermediate portion 44 progressively changes from substantially circular, as in section BB, to an elongated shape having two substantially flat or linear opposing sidewalls 52a, 52b. As can be appreciated, the elongation progressively increases in a first dimension "h1", while progressively narrowing in a second dimension "w1". Thus, the distance between opposing linear walls 52a and 52b is less than the distance between opposing arcuate walls 54a and 54b as shown in FIGS. 14C, 14D and 14E, with these distances increasing toward rear section 42, represented by h2 and w2 in cross-section DD and h3 and w3 in cross-section EE. In summary, h1<h2<h3 while w1>w2>w3, with "h" designating the major diameters and "w" designating the minor diameters.

Rear portion 42 can be considered to begin, for convenience, at section line EE and terminate at the proximalmost edge 48 of tip 30. The rear portion 42 preferably has the same elongated cross-sectional dimension throughout its length, with substantially linear walls 52a and 52b separated by a distance w4 smaller than distance h4 between opposing curved walls 54a and 54b. However, preferably h4=h3 and w4=w3.

Distances w and h for various size tips are provided by way of example in Chart II:

CHART II

| Tip Size | w1 | w2 | w3 | w4 | h1 | h2 | h3 | h4 |
|---|---|---|---|---|---|---|---|---|
| 1.5 mm | .041 | .038 | .034 | .034 | .051 | .054 | .058 | .059 |
| 2.0 mm | .057 | .054 | .046 | .046 | .067 | .070 | .078 | .079 |

CHART II-continued

| Tip Size | w1 | w2 | w3 | w4 | h1 | h2 | h3 | h4 |
|---|---|---|---|---|---|---|---|---|
| 2.5 mm | .069 | .064 | .057 | .057 | .085 | .089 | .097 | .098 |
| 3.0 mm | .085 | .082 | .068 | .068 | .101 | .104 | .117 | .118 |

As can be appreciated, for larger or smaller tips, distances "h" and "w" would vary, but preferably the ratio of h3 to w3 in the rear portion would remain approximately the same, namely about 55% to about 65%.

Obviously other dimensions and ratios than those provided above are also contemplated as long as the objectives of the present invention are maintained.

It should also be appreciated that the front, intermediate and rear portions/sections are designated for convenience and are not intended to denote three separate segments connected together. Tip 30 is preferably a monolithic piece.

With reference to FIGS. 9–11, tip 30 has a proximal or rear opening 32 and a front opening 34 connected by lumen 36, which narrows to lumen 38. The flexible shaft 22 is inserted through rear opening 32 and attached to the tip 30 within lumen 36 (see FIG. 5). A guidewire (not shown) extends through the hollow flexible shaft 22, narrowed lumen 38 and through front opening 34 to enable over the wire insertion of the atherectomy tip. One or more side ports (not shown), similar to the side port 80 of the later described embodiment of FIG. 15 could be provided to enable removal of the plaque.

A scalloped or narrowed section 57, 59 is formed in the intermediate section 44 to reduce the profile of the tip 30. These scalloped sections form the aforedescribed opposing substantially linear walls shown in the cross sectional views of FIGS. 14A–F. As will become apparent from the discussion below, by reducing the profile, i.e. the diameter and circumference, the atherectomy tip of the present invention could be inserted through smaller introducer sheaths than would otherwise be the case if the circumference increased with increasing diameter.

The region of plaque removal is defined by the largest diameter region of the tip since the tip is rotating at high speeds and the plaque is cut or abraded only where the tip comes into contact with it. However, the sheath size required is determined by the largest circumference region of the tip.

More specifically, in the prior art elliptical tip described above, the largest diameter region is circular in cross-section so the diameter is constant in all radial directions. Thus, the area of plaque removal is defined by this diameter. However, in this prior art elliptical tip, the circumference gradually increases from the distal portion to the intermediate portion. Thus, this larger circumference area at the greatest diameter portion dictates the size of the introducer sheath needed to accommodate the tip.

In the atherectomy tip of the present invention, and with reference to FIGS. 6–8, the largest diameter area, D2, is at the intermediate portion and likewise defines the region of plaque removal. However, the circumference does not progressively increase as the circumference C2 at this largest diameter region is equal to the circumference C1 at the distal/intermediate transition portion. Thus, by scalloping or narrowing the portions 57, 59 of the tip 30 to create a circumference C2 equal to the circumference C1, an introducer sheath can be utilized that effectively only needs to accommodate circumference C1. Stated another way, for a given major diameter at the largest region of the tip, the circumference C2 of the present invention is smaller than a corresponding circumference of the prior art elliptical tip.

As a result of these scalloped sections, as the diameter of tip 30 increases in one orientation, it decreases in the transverse orientation, enabling the circumference to remain constant. Since the diameter is reduced in one transverse orientation, the tip 30 can be introduced into an introducer sheath have an internal diameter slightly less than the largest diameter of the tip, i.e. slightly less than D2, since the sheath has room to deform because of the reduced regions, i.e. the scalloped sections, of the tip 30. In the prior art elliptical tip, the rounded symmetrical configuration leaves no room for the sheath to deform so the sheath size must exceed the largest diameter region.

To better appreciate how the tip 30 of the present invention can be utilized with smaller sized sheaths, Chart III comparing the tip 30 of the present invention to the prior art elliptical tip is set forth below. The tip diameter corresponds to the largest diameter region of the elliptical tip of the prior art as depicted in FIG. 1 and the largest diameter region of the tip 30 of the present invention depicted as D2 in FIG. 7.

CHART III

| Tip Diameter | Sheath Diameter For Prior Art Tip | Sheath Diameter for Tip 30 of Present Invention |
|---|---|---|
| 1.5 mm | 5 French (1.67 mm) | 4 French (1.35 mm) |
| 2.0 mm | 7 French (2.3 mm) | 6 French (2.0 mm) |
| 2.5 mm | 8 French (2.7 mm) | 7 French (2.3 mm) |
| 3.0 mm | 10 French (3.3 mm) | 8 French (2.7 mm) |

As can be appreciated, the tip 30 of the present invention can fit into conventional introducer sheaths having an internal diameter less than the largest outer diameter of the tip 30. This can be achieved by the fact that the tip 30 can deform the internal walls of the sheath as it is inserted, by elongating it in the direction shown in FIGS. 5 and 7. If the scalloped walls were not provided, the sheath could not deform because it would be limited by the width of the tip as described below.

Another way to view the advantage of the tip 30 of the present invention is that for a given catheter French size desired to be used by the surgeon, a larger atherectomy tip can be utilized if the atherectomy tip 30 of the present invention is selected instead of the prior art elliptical tip, thereby advantageously increasing the region of plaque removal to create a larger passageway in the vessel.

Alternate embodiments of the tip 30 are shown in FIGS. 15A and 15B. These tips are identical to tip 30 except for the longitudinal cutting grooves 84, 86 and 89 of FIGS. 15A and 15B, the elongated, circular and oval cutting grooves 96 of FIG. 16 and the provision of side port 80 in FIG. 15. The grooves/cutouts provide a roughened surface to cut or ablate the plaque as the tip is rotated. Details of these tips and grooves are described in parent application Ser. No. 09/629, 313, the entire contents of which are incorporated herein by reference.

In short, tip 70 of FIGS. 15A and 15B has a front portion 71, a rear portion 72 and an intermediate portion 74 scalloped (narrowed) at region 76 to form reduced profile substantially flattened walls 78 in the same manner as tip 30. Side port 80, communicates with certain cutouts formed in the tip to provide an outlet for the removed plaque and deposits. Internal lumen 82 is configured to receive a guidewire extending through distal opening 83. The cross-sectional configuration of tip 70 is identical to tip 30, except for the grooves 84, 86 and 89 on the outer surface and the side port 80. As shown, cutting grooves 84, 86, and 89 all begin adjacent nose 75, however they terminate at different regions. That is, grooves 89 terminate at edge 88 at intermediate portion 74 adjacent scalloped region 76; grooves 84 terminate at edge 79 in intermediate portion 74; and grooves 86 terminate at edge 87 in rear portion 72.

In the alternate embodiment of FIG. 16, tip 90 similarly has a front portion 91, intermediate portion 92 and rear portion 94. Scalloped region 95 forms a reduced profile substantially flattened wall 97. Internal lumen 93 is configured to receive a guidewire. The cross sectional configuration of tip 90 is likewise identical to tip 30, except for the grooves/cutouts on the outer surface. As shown, the circular, oval and elongated cutouts are interspersed in the front intermediate and rear portions of tip 90.

FIGS. 17A–17D illustrate another embodiment of the tip of the present invention formed with grooves by a laser cutting technique. Tip 100 of FIGS. 17A–17D is identical to tip 30 in all respects except for the provision of the grooves or indentations 103. The grooves 103 are formed by laser cutting a series of grooves extending longitudinally within the interior of the tip stock. The tip is then ground to remove portions of the outer surface to partially communicate with the grooves, thereby creating indentations forming a roughened surface for contact with the plaque. The resulting formation is a series of elongated cutouts/indentations on the front and intermediate portions 101, 104 and oval shaped cutouts/indentations on the distal and intermediate portions 102, 104. As in the other embodiments, the tip 100 has an internal lumen 106 terminating at distal opening 107 in bullet shaped nose 109 for a guidewire. Scalloped (narrowed) sections 110, 112 are identical to those of tip 30 and the cross-sectional configurations are also identical except for the cutouts.

Another way contemplated to create the roughened surface is by blasting, e.g. sandblasting or grit blasting, the tip. The tip is held in a fixture and blasted at a certain pressure, thereby removing portions of the outer surface to create a roughened surface. Creation of a roughened surface by chemical etching is also comtemplated.

Use of the atherectomy tip of the present invention is illustrated in FIGS. 18–20. Although tip 70 of FIG. 15 is shown, it should be understood that atherectomy tips 30, 90 and 100 are used in the same manner. As shown in FIG. 18, plaque "P" buildup on the interior wall of the vessel "V" has occluded the passageway through the vessel. Tip 70 is inserted over guidewire 60 and via flexible rotatable shaft 22, is rotated at high speed in the direction of arrow X in FIG. 19 to remove plaque which comes into contact with its outer surface. The removed plaque which enters through the grooves in tip 30 is removed through side port 80 and removed from the body.

FIG. 21 illustrates an embodiment of the atherectomy tip of FIG. 9, designated generally by reference numeral 130, having a side opening 159 in distal portion 140 and intermediate scalloped portion 144 to facilitate removal of the abraded plaque debris in the direction of the arrows. An aspiration device can be utilized to suction the cut plaque. One example of an aspiration device is the Oasis device, sold by Boston Scientific, Corp. and designated by reference numeral 200 in FIG. 22. (Only the distal end of the device is shown) The device includes an aspiration lumen 202 and a hook-shaped fluid dispenser 204 to deliver saline to help direct the debris through aspiration lumen 202. Clearly, the devices of the present invention can be utilized with other aspiration devices.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A surgical apparatus for removing deposits from an interior of a vessel comprising;

a rotatable shaft;

a rotatable tip having a longitudinal axis and mounted to the rotatable shaft, the tip being rotatable about its longitudinal axis upon rotation of the shaft to remove deposits from the interior of the vessel, the tip further having a distal portion, a proximal portion and an intermediate portion between the distal and proximal portions, the intermediate portion defined by a plurality of transverse cross-sectional areas, each transverse cross-sectional area defining first and second axes substantially perpendicular to each other to define a width dimension along a first axis and a height dimension along the second axis, the height dimension being greater than the width dimension.

2. The surgical apparatus of claim 1, wherein the height progressively increases towards the proximal portion and the width progressively decreases toward the proximal portion.

3. The surgical apparatus of claim 2, further comprising an opening in a sidewall of the tip for aspiration of removed deposits.

4. The surgical apparatus of claim 1, wherein the distal portion has a bullet shaped nose.

5. The surgical apparatus of claim 2, further comprising a plurality of longitudinally extending grooves formed in an outer surface of the tip to form an ablation surface.

6. A surgical apparatus for removing deposits such as plaque from an interior of a vessel, comprising:

a rotatable shaft having a lumen extending therethrough dimensioned to receive a guidewire;

a tip having a longitudinal axis and mounted on the rotatable shaft for rotation about its longitudinal axis upon rotation of the shaft, the tip having a distal portion, a proximal portion and an intermediate portion between the distal and proximal portions, the tip including a guidewire lumen for receiving a guidewire to enable over the wire insertion of the shaft and tip, the distal portion of the tip being substantially circular in cross-section and the intermediate and proximal portions being non-circular in cross-section.

7. The surgical apparatus of claim 6, wherein the non-circular cross-section of the intermediate and proximal portions is defined by first and second opposing walls separated by a first distance and third and fourth opposing walls separated by a second distance, the first distance being greater than the second distance.

8. The surgical apparatus of claim 7, wherein the first distance progressively increases towards the proximal portion and the second distance progressively decreases towards the proximal portion.

9. The surgical apparatus of claim 8, wherein the third and fourth walls have a substantially linear portion.

10. The surgical apparatus of claim 9, wherein the first and second walls are curved.

11. The surgical apparatus of claim 10, wherein the distal portion has a bullet nose configuration.

12. The surgical apparatus of claim 7, further comprising an opening in a sidewall of the tip for removing the removed deposits.

13. The surgical apparatus of claim 7, further comprising a plurality of longitudinally extending cutting grooves formed in an outer surface of the tip.

14. A vascular surgical apparatus for removing deposits such as plaque from a vessel comprising:

a rotatable shaft with a distal section;

a distal tip mounted on the distal section and rotatable upon rotation of the shaft to remove deposits in a circumferential area determined by a major diameter of the distal tip as it rotates on its axis, wherein the distal tip has a proximal portion, a distal portion and an intermediate portion between the proximal and distal portions, wherein each transverse cross-section of the tip defines a circumference, a first diameter, and a second diameter substantially orthogonal to the first diameter, the first diameter of the intermediate portion being greater than the first diameter of the distal portion and the circumference at the distal portion being substantially equal to the circumference at the intermediate portion.

15. The surgical apparatus of claim 14, wherein the first diameter of the intermediate portion is greater than a second diameter of the intermediate portion.

16. The surgical apparatus of claim 15, wherein the intermediate portion has opposing scalloped portions to form the smaller second diameter region.

17. The surgical apparatus of claim 15, wherein the first diameter of the distal portion is substantially equal to the second diameter of the distal portion.

18. The surgical apparatus of claim 17, wherein the smaller second diameter is formed by opposing scalloped regions of the intermediate and proximal portions.

19. The surgical apparatus of claim 12, further comprising a plurality of longitudinally extending cutting grooves formed in an outer surface of the distal tip.

20. A surgical apparatus for removing deposits from an interior of a vessel, comprising:

a rotatable shaft having a lumen extending therethrough dimensioned to receive a guidewire;

a distal tip having a longitudinal axis and mounted on the rotatable shaft and rotatable about its longitudinal axis upon rotation of the shaft to remove deposits in an circumferential area determined by a major diameter of the distal tip as it rotates on its axis, the tip having a distal portion, a proximal portion and an intermediate portion between the distal and proximal portions, the distal tip including a guidewire lumen for receiving a guidewire, the distal portion being circular in cross-section and the intermediate and proximal portions being non-circular in cross-section, the non-circular cross section defined by first and second opposing curved walls defining a first distance therebetween, and third and fourth opposing walls each having a substantially straight side and defining a second distance therebetween, wherein the first distance is greater than the second distance, and wherein each transverse cross-section of the tip defines a circumference, the first distance between opposing walls of the intermediate section being greater than the first distance between opposing walls of the distal section and the circumference at the distal section being equal to the circumference at the intermediate portion.

21. A method for removing deposits from an interior of a vessel comprising the steps of:

providing an introducer sheath having a first internal diameter;

providing a deposit removal tip having a rotating shaft and a rotating tip at the distal end of the shaft, the rotating tip having an outer diameter greater than the internal diameter of the sheath and further having first and second opposing narrowed regions;

inserting the introducer sheath through a skin incision and into a vessel, the introducer sheath forming an incision opening at least equal to the external diameter of the sheath;

inserting the rotating tip into the introducer sheath to deform the introducer sheath to accommodate the larger outer diameter of the rotating tip;

inserting the tip out through a distal opening in the introducer sheath, thereby allowing the introducer sheath to return to its undeformed configuration;

advancing the distal tip adjacent the deposits to be removed; and rotating the tip at high speed to contact and remove the deposits from the vessel.

22. The method of claims 21, further comprising the step of inserting the tip over a guidewire.

23. The method of claim 22, further comprising the step of removing the deposits through a side port in the tip.

* * * * *